(12) United States Patent
Mark

(10) Patent No.: US 6,537,239 B2
(45) Date of Patent: Mar. 25, 2003

(54) INSERT FOR A NOZZLE OF A FLOW THROUGH LIQUID APPLICATOR AND COMBINATION THEREOF

(76) Inventor: Phillip Mark, 1255 LaQuinta Dr., Suite 214A, Orlando, VA (US) 32809

( * ) Notice: Subject to any disclaimer, the term of this patent is extended or adjusted under 35 U.S.C. 154(b) by 0 days.

(21) Appl. No.: 09/853,772

(22) Filed: May 14, 2001

(65) Prior Publication Data

US 2002/0166903 A1 Nov. 14, 2002

(51) Int. Cl.$^7$ .............................................. A61M 35/00
(52) U.S. Cl. ........................... 604/2; 443/80; 443/81; 443/89; 443/224
(58) Field of Search ........................... 604/1, 2, 310, 604/311; 433/80, 81, 89, 224

(56) References Cited

U.S. PATENT DOCUMENTS

| | | | | |
|---|---|---|---|---|
| 830,872 A | * | 9/1906 | Arthur | 433/83 |
| 3,896,552 A | * | 7/1975 | Russell | 433/136 |
| 4,233,025 A | * | 11/1980 | Larson et al. | 433/136 |
| 5,033,650 A | * | 7/1991 | Colin et al. | 222/137 |
| 5,236,355 A | * | 8/1993 | Brizzolara et al. | 433/80 |
| 5,269,684 A | * | 12/1993 | Fischer | 433/90 |
| 5,387,103 A | * | 2/1995 | Fischer | 433/89 |
| 5,401,169 A | * | 3/1995 | Fleisher et al. | 433/90 |
| D377,216 S | * | 1/1997 | Mark | D24/152 |
| D377,526 S | * | 1/1997 | Mark | D24/152 |
| D378,235 S | * | 2/1997 | Mark | D24/152 |
| D385,964 S | * | 11/1997 | Mark | D24/176 |
| D392,465 S | * | 3/1998 | Mark | D4/114 |
| D403,768 S | * | 1/1999 | Mark et al. | D24/152 |
| D409,914 S | * | 5/1999 | Mark | D9/436 |
| D417,394 S | * | 12/1999 | Mark | D9/436 |
| 6,030,214 A | * | 2/2000 | Zwingenberger | 433/82 |
| 6,059,570 A | * | 5/2000 | Dragan et al. | 433/80 |
| 6,083,002 A | * | 7/2000 | Martin et al. | 433/90 |
| 6,234,795 B1 | * | 5/2001 | Fischer | 433/90 |
| 6,238,120 B1 | * | 5/2001 | Mark | 401/265 |
| D450,836 S | * | 11/2001 | Mark | D24/119 |
| 6,334,774 B1 | * | 1/2002 | Mark | 433/89 |
| 6,343,929 B1 | * | 2/2002 | Fischer | 433/81 |
| 6,376,025 B1 | * | 4/2002 | Mark | 427/462 |
| 6,382,972 B1 | * | 5/2002 | Fischer et al. | 433/90 |
| 6,450,810 B1 | * | 9/2002 | Fischer et al. | 433/80 |
| 6,467,982 B1 | * | 10/2002 | Tsao | 401/263 |

\* cited by examiner

*Primary Examiner*—Weilun Lo
*Assistant Examiner*—Michael G. Bogart
(74) *Attorney, Agent, or Firm*—Eric P. Schellin

(57) ABSTRACT

The present invention pertains to two inserts to be used in conjunction with the nozzles of known liquid flow through applicators. The inserts have a proximate flange detailed to fit into a wider portion of the applicator and a bristle or dabber portion at its distal end detailed to extend beyond the applicator. The bristle or dabber portions are connected by an elongated rod portion. In one embodiment the rod portion is crisscrossed with a clockwise thread and a counter-clockwise thread whereby two disparate liquids may be mixed together through the flow transitory passage of the liquids in the nozzle. In the second embodiment the rod portion is essentially smooth. However, the external diameter of the rod is substantially less than the internal diameter of the passage of the applicator whereby an annular space is formed.

5 Claims, 2 Drawing Sheets

FIG. 1
FIG. 2
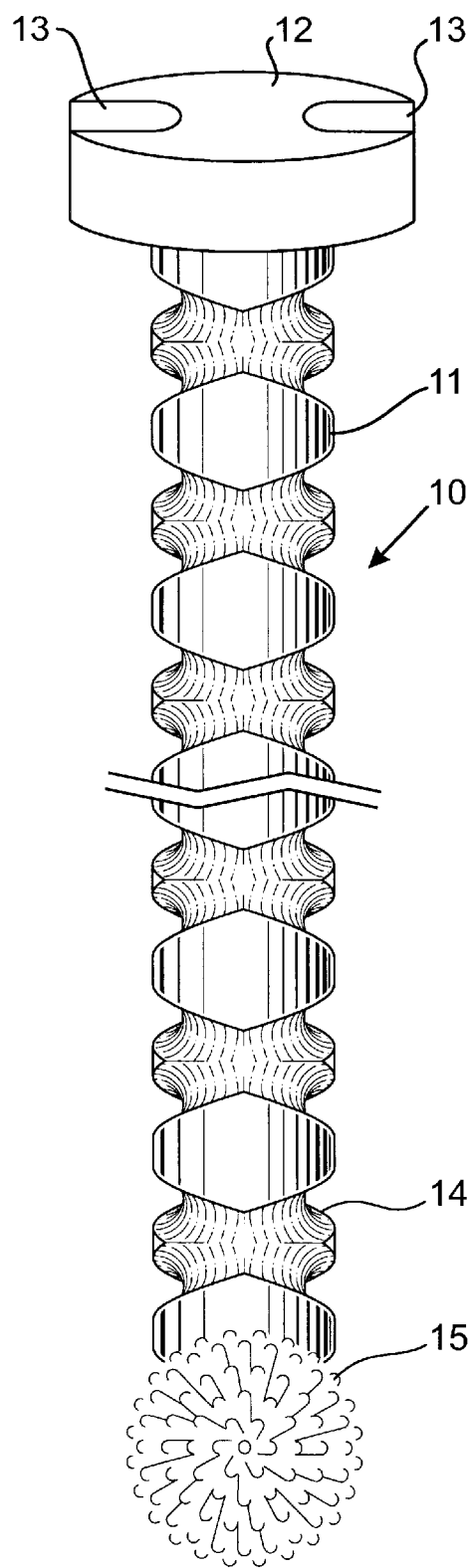
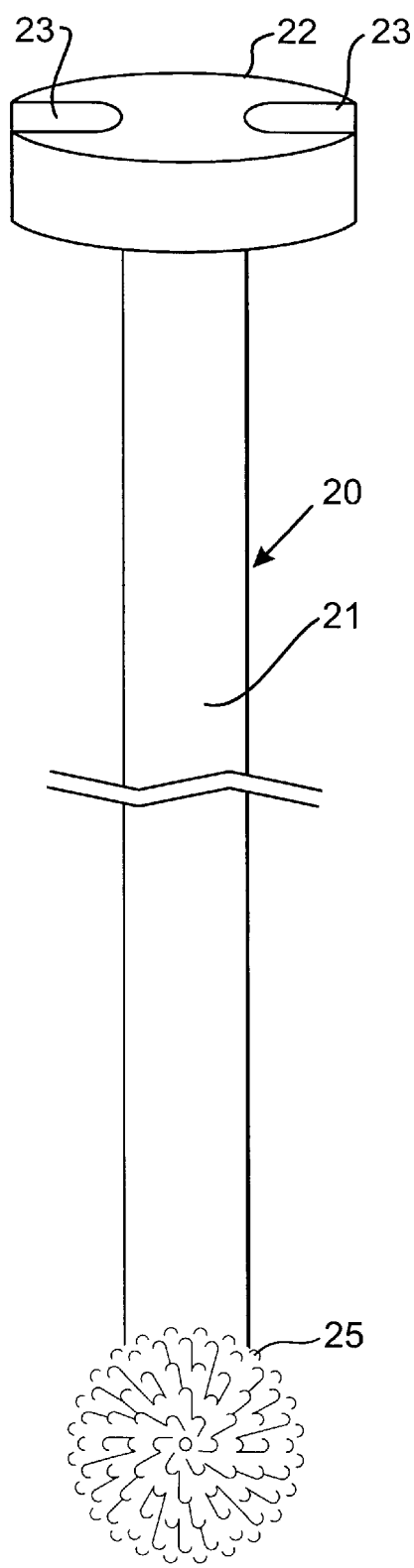

INSERT FOR A NOZZLE OF A FLOW THROUGH LIQUID APPLICATOR AND COMBINATION THEREOF

FIELD OF THE INVENTION

A liquid flow through applicator for application of selected liquids to the surface, for instance, medicaments to the teeth, lubricants to diminutive machine parts, and adhesives to be-adhered parts by hobbyists.

BACKGROUND OF THE INVENTION

A considerable number of patents have been granted where the subject matter is a conventional syringe with a nozzle as attachment where the nozzle terminates at its distal end in a simple tube, a tube cut an angle or in a tuft of bristles or a foamed flow through appendage. The present inventor has a number of applicable patents, for instance, Nos. D441,074 and D441,073, all of which are incorporated herein in their entirety by reference.

SUMMARY OF THE INVENTION

The invention is an insert for the extending tube of a nozzle of a flow through applicator. The insert consists of a elongated rod-like member which has at its proximate end a radially extending concentric flat disc. The disc has a plurality of notches through which liquid can flow. The underside of the flat disc is detailed to abut against the inside shoulder of a nozzle at the point where the elongated tube begins.

The said rod-like member is of a length whereby it extends beyond the opening of the distal opening of the elongated tube of the nozzle. The rod terminates at its distal end in a bristle tuft in-one embodiment and in a foam dabber in another embodiment.

The elongated rod-like member in one embodiment has an external diameter that is relatively smaller than the internal diameter of the elongated tube of the said nozzle. In a second embodiment the rod-like member be substantially the same as the internal diameter of the elongated tube of the nozzle. However, this second embodiment possesses a clock-wise thread and a counter a counter-clock-wise thread which criss-cross.

The second embodiment is designed to admit two liquids that are maintained separately until applied to the point of use. The second embodiment by having the criss-crossing threads whereby the disparate liquids are mixed as they flow along the threads of the insert.

BRIEF DESCRIPTION OF THE INVENTION

FIG. 1 is a side view of a first embodiment of the insert of the present invention.

FIG. 2 is a side view of a second embodiment of the insert of the present invention.

DETAILED DESCRIPTION OF THE INVENTION

Figure 3:
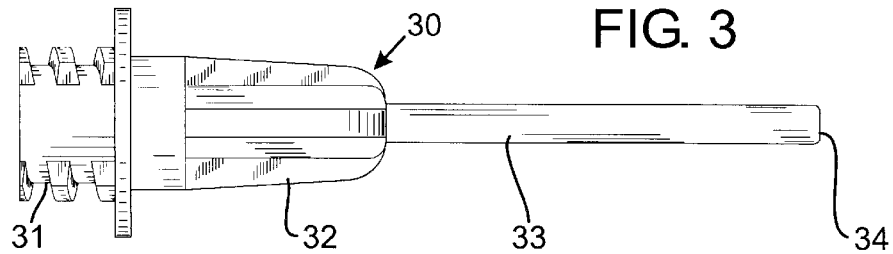
FIG. 3 is a side view of a prior known flow through liquid applicator.

Attention is directed to FIG. 1 for a detailed description of one embodiment of the invention, shown, generally by reference 10. The insert comprises an elongated rod 11 which terminates at the proximate end with a disc 12. The disc 12 has a plurality of notches 13. The rod 11 is threaded at 14 in a clockwise manner and also in a counter-clockwise manner. The rod 11 terminates at its distal end in a tuft of bristles 15.

A second embodiment of the insert is shown, generally, by reference 20. This embodiment is like the infra discussed embodiment but the rod 21 is of a smooth surface and is seen not to be threaded. It also has a proximately located disc 22, notches 23 and terminates at its distal end in a bristle tuft 25.

Figure 6:
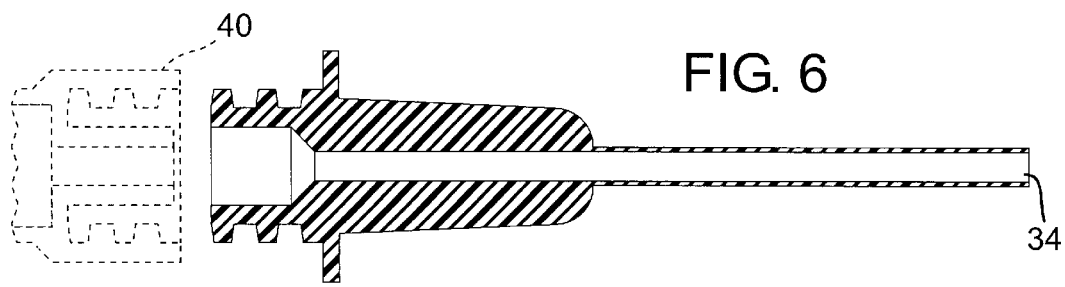
FIG. 6 is cross-sectional view of the flow through liquid applicator shown in FIG. 3 with the distal end portion shown in dotted lines.

FIGS. 3 and 6 show a side view of a known liquid applicator 30 with which the inserts of the present invention are to be used. The applicator 30 has a proximal male threaded tubular end 31. The said tubular end 31 is integral with an elongated tubular continuation 32. The latter terminates distally in an elongated relatively then tube 33 and has a distal orifice 34.

FIG. 6 shown in dotted lines a portion of a syringe 40 to which the applicator can be affixed as by screwing the applicator into a threaded socket of the syringe.

Figure 4:
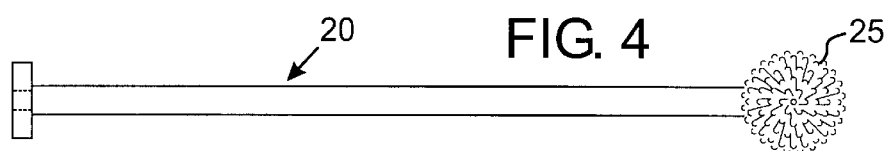
FIG. 4 is another side view of the second embodiment of the insert of the present invention.
Figure 7:
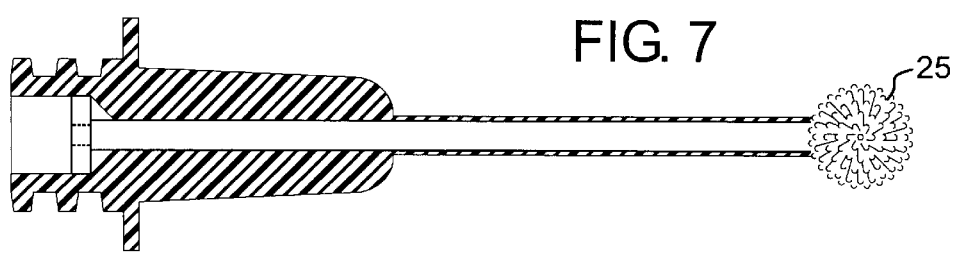
FIG. 7 is a cross sectional view of a flow through liquid applicator with the insert of FIG. 4 in place.

Attention is now directed to FIG. 7 for a view of the insert 20 of FIG. 4 in an inserted position in the applicator. The insert is positioned by inserting it bristles first into the tubular end 31 then passing the bristles and remainder of the insert through the continuation 32 and down the length of tube 33 until the disc underside abuts against the bottom of the tubular end 31 as depicted in FIG. 7. The rod 21 of the insert is of sufficient length whereby the tuft bristles 25 extend beyond the orifice 34 of the tube 33. The rod is of a diameter smaller than the internal diameter of the continuation 32 and tube 33 thereby provides a concentric annular space, 26 around the insert rod 21. Fluid that is forced fed into the annular end 31 flows abut the disc 22 through notches 23 and the annular space 26 in continuation 32 and tube 33 to discharge from orifice 34 and onto the tuft of bristles 25.

Figure 5:
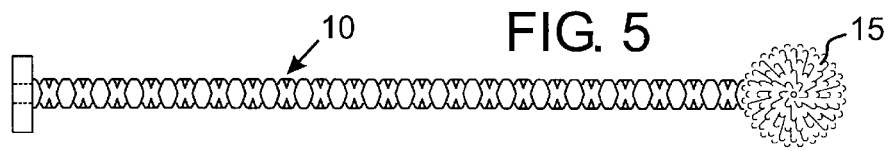
FIG. 5 is another side view of the first embodiment of the insert of the present invention.
Figure 8:
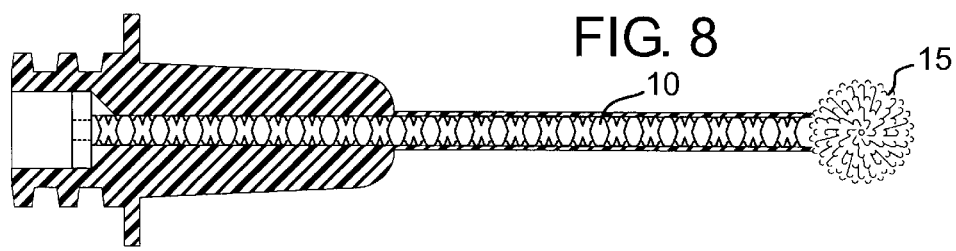
FIG. 8 is a cross sectional view of a flow through liquid applicator with the insert of FIG. 5 in place.

Attention is now directed to FIG. 8 which is similar to FIG. 7 except that the insert of FIGS. 1 and 5 is shown to be in place. In this fashion the flow through liquid applicator is screwed into a two part syringe that is able to contain two liquids in a separated condition such as a monomers plastic and a hardener therefore until about to be employed.

The two liquids are sparged into the tubular end 31 of the applicator 30. The liquids flow through the said notches of the disc 12 of insert 10. One of the liquids is directed to flow through one notch and follow, for instance, the path of the clock-wise thread. The other, to be mixed liquid, flows through the oppositely disposed notch and then through the path defined by the counter clock-wise thread. As the two threads criss-cross the liquids are mixed as they confluence with one another, whereby the time they reach the bristles at the distal end the liquids are throughly mixed.

The bristles depicted at the end of the inserts 10 and 20 are stylized in the rendition in the drawings. As has been stated heretofore, elastomeric foam dabbers may be employed in place of the bristles.

It is contemplated that inserts 10 and 20 may be made of a plastic material such as, polyethylene or polypropylene. They may also be constructed of metal for greater rigidity.

The great usefulness of the said inserts of the present invention resides in the fact that the threaded insert 10 is used for mixing two liquids while insert 20 can be used for a single liquid.

What is claimed is:

1. In a liquid flow through nozzle for a syringe comprising a proximate tubular portion terminating in an elongated tube distal portion the proximate tubular portion being of an internal diameter substantially larger than the internal diameter of the distal portion, said nozzle having an insert, said insert having at its proximate end a disc member and positioned in said proximate tubular portion, said disc having at least one notch therethrough, said disc having an elongated rod extending from said disc through the elongated tube distal portion, said elongated rod extending beyond said nozzle and terminating in a dabber.

2. The nozzle of claim 1 wherein the elongated rod has a clockwise thread and a counter clockwise thread, said disc has two oppositely disposed notches.

3. The nozzle of claim 1 wherein elongated rod has an external diameter smaller than an internal diameter of the distal elongated tube whereby there is an annular space between said elongated rod and said distal elongated tube.

4. The nozzle of claim 2 wherein the dabber at the distal end of the insert comprises bristles.

5. The nozzle of claim 3 wherein the dabber of the distal end of the insert comprises an elastomeric foam member.

* * * * *